United States Patent [19]

Neümeister et al.

[11] Patent Number: 4,560,352
[45] Date of Patent: Dec. 24, 1985

[54] DISPENSER FOR METERING DENTAL COMPOSITIONS

[75] Inventors: Alexander Neümeister, Munich; Wolf-Dietrich Herold, Hechendorf, both of Fed. Rep. of Germany

[73] Assignee: ESPE Fabrik Pharmazeutischer Präparate GmbH, Fed. Rep. of Germany

[21] Appl. No.: 548,830

[22] Filed: Nov. 4, 1983

[30] Foreign Application Priority Data

Nov. 4, 1982 [DE] Fed. Rep. of Germany ....... 3240785

[51] Int. Cl.⁴ .............................................. A61C 5/04
[52] U.S. Cl. .................................... 433/90; 222/390; 604/224
[58] Field of Search ....................... 433/81, 84, 90, 89; 222/390, 191, 81; 604/224, 227, 233

[56] References Cited

U.S. PATENT DOCUMENTS 936,101 10/1909 Edwards ............................ 222/390
4,198,756 4/1980 Dragan .
4,479,781 10/1984 Herold et al. ....................... 222/390

FOREIGN PATENT DOCUMENTS 2741185 9/1977 Fed. Rep. of Germany .
2212768 7/1974 France .

Primary Examiner—1
Assistant Examiner—Robert Peshock
Attorney, Agent, or Firm—Barnes & Thornburg

[57] ABSTRACT

A one-hand operated dispenser for metering dental compositions comprises a casing for accommodating the dental composition between a forward dispensing opening and a plunger which is slidable within the casing. The plunger is advanced by means of a threaded spindle which engages in a nut mounted at the casing rear end so as to be secured against rotation and axial displacement. The casing rear end is rotatably supported within a sleeve which in turn is detachably inserted in a handle. The sleeve is formed with an axially extending slot through which a finger is visible which is disposed at the rear end of the spindle. When the handle is gripped, the casing may be rotated between the thumb and index finger such that the spindle advances the plunger thereby urging the dental composition out of the dispensing opening. During the forward movement of the spindle the finger travels forwardly in the axially extending slot and indicates the level of the dental composition.

16 Claims, 2 Drawing Figures

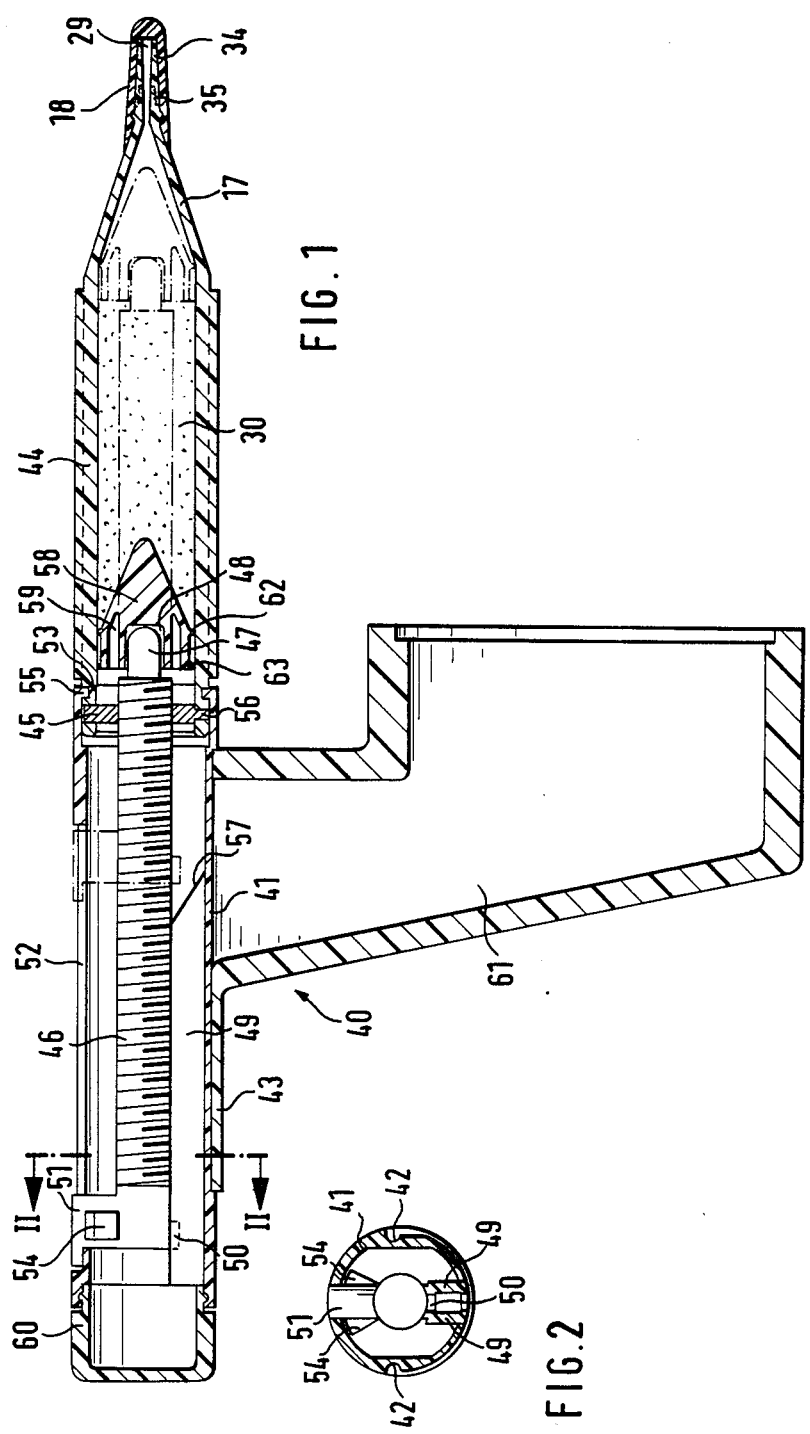

DISPENSER FOR METERING DENTAL COMPOSITIONS

DESCRIPTION

This invention relates to a one-hand operated dispenser for metering dental compositions.

In dental practice, when dental prosthetic parts are made in laboratory and during the preservative treatment in situ, plastics compositions are used among other materials, which are initially paste-like and moldable and are subsequently cured by photopolymerization in their final molded shape.

Normally, such compositions are supplied by the manufacturer in tins out of which they are applied by means of a spatula or brush. In order to prevent premature photopolymerization it is necessary to seal the stock tins immediately upon each removal of material to protect the compositions against incident light. Experience has shown, however, that normally this is not done, especially in a dental laboratory when larger dental prosthetic parts are processed, because it would mean that the application tool has to be put down time and again, thus resulting in an increase of labor.

Furthermore, work is normally done with several differently colored compositions so as to achieve the shade of the natural teeth as accurately as possible. When, as is usual, quantities of the different compositions are successively taken out with the same application tool, an undesirable mutual carryover and mixing of the differently colored compositions will occur. In addition to the surface polymerization discussed above, which is unavoidable in actual practice, this color contamination also has the effect that the compositions will prematurely become useless.

In view of these problems, a device had been proposed which can be made of few and inexpensive parts and is easily manipulated and with which dental compositions, in particular photopolymerizable compositions, may be dispensed with one hand in accurately metered quantities and applied directly onto the location that is to be processed. The dental composition is exposed only at the exit opening of the casing, which has a correspondingly small diameter already for reasons of fine metering and selective dispensing onto small surfaces to be processed. Thus, photopolymerization may occur at most at the small surface that is exposed within the dispensing opening. Moreover, in thin layers the polymerization is inhibited by the presence of atmospheric oxygen, so that the composition at the dispensing opening will not be cured significantly and will in any case remain easily displaceable and dispensable. The use of this device furthermore eliminates a carryover and mutual contamination of a plurality of compositions, which occurs when the usual tins and brushes are employed.

The design according to the earlier proposal results in a simple one-hand manipulation due to the fact that the entire device need merely be gripped by the handle, and nothing but a turning of the casing relative to the handle is required, wherein the relative axial position of handle and casing does not change during operation.

The earlier device can be dismantled into two parts, one part containing the dental composition and being replaced after consumption thereof by a corresponding freshly filled part, whereas the other part is a manipulating part which may be reused again and again. The separate structure is advantageous because normally a large number (e.g. 50) of dental compositions of different shades are kept in readiness out of which the dentist or dental technician requires only a few (typically three) for each work, so that only a correspondingly small number of manipulating parts has to be available into which the respectively required device part containing the dental composition is inserted.

The present invention has for its object to provide—while retaining the advantages of the earlier proposal—a configuration for the device which may be dismantled into two parts and assembled therefrom in a manner even simpler to the user.

In view of this object, the dispenser for metering dental compositions according to the present invention comprises (a) a casing with a dispensing opening,
(b) a plunger movable within said casing, the space defined between the plunger and said dispensing opening serving to accomodate the dental composition,
(c) a threaded spindle which acts on said plunger and is axially movable relative to said casing,
(d) a nut fixed to said casing and being rotatable relative to said spindle for advancing the same,
(e) a sleeve member surrounding said spindle and including means for supporting said spindle non-rotatably but axially movably and means for retaining said casing rotatably but axially not movably, and
(f) a handle detachably joined to said sleeve member.

While the earlier device achieves the dismantling by separating the manipulating member as a whole from the assembly containing the dental composition and formed by the casing, the nut and the threaded spindle, which means that the two parts interengage while being in part rotatable relative to each other, in the present case the dismantling is effected into two parts, namely a handle and a sleeve member, which parts are immovable relative to each other when assembled. Thus, these two parts need only be brought into a fixed position relative to each other. Apart from the simplified manipulation this also means that the joint is subject to less wear and that such wear in any case does not influence the operability of the device.

According to a preferred embodiment, the said joint is a simple snap connection. Further developments of the invention provide for a good axial guiding of the non-rotatably secured spindle, which is all the more important the greater the length of the casing accommodating the dental composition and thus the entire stroke of the spindle.

According to a further modification, the spindle additionally serves as a level indicator so that the user may be informed of the respectively available quantity of the dental composition.

According to a further advantage of the invention, the entire axial length of the housing is available for performing the rotary movement.

Using left-hand threads for the spindle and nut is especially beneficial when the device is operated with the right hand.

Further developments of the invention ensure a good view towards the processing site, at the same time minimizing the surface of the dental composition possibly exposed to light when the device is put down, and adapt the device for direct in situ application of the composition.

A preferred embodiment of the invention will be explained in detail below with references to the drawing, in which:

FIG. 1 is a longitudinal sectional view through the device, and

FIG. 2 is a cross-sectional view along the line II—II of FIG. 1.

The dispensing device shown in the drawing comprises a manipulating member generally referenced 40 including two detachably joined component parts, viz., a sleeve 41 and a handle 61. As will be apparent from FIG. 2, the sleeve 41 is of substantially circular cylindrical shape and is formed on the outside thereof with two horizontal and approximately diametrically opposed indentations 42 into which the handle 61 snap-engages by means of two complementary protuberances (not shown) such that the sleeve 41 and the handle 61 may be connected to each other so as to be non-rotatable and secured against displacement. The protuberances are provided on the outer ends of a part-cylindrical shell 43 the inner diameter of which corresponds to the outer diameter of the sleeve 41.

An inwardly projecting annular ring at the forward end of the sleeve 41 engages in an annular groove 53 formed in the vicinity of the rearward end of a cylindrical casing 44 such that the casing 44 is rotatable relative to the sleeve 41 while it is secured against axial movement. A nut 45, which is secured against rotation relative to the casing 44 by means of a bottom lug 56, is inserted into a slot open towards the top and formed at the rear end of the casing 44. A threaded spindle 46 engaging the nut 45 is formed at its front end with a rounded, reduced diameter extension 47 adapted to be plugged into a recess 48 formed in the rear face of the plunger 58. The recess 48 is surrounded by an annular recess 59 also open towards the rear and imparting elasticity to sealing rings 62 and 63 so that these ensure impermeability over the entire stroke path of the plunger 58. The plug-in connection causes central guiding of the spindle 46 in the axial direction by the plunger, which is particularly important when the plunger 58 is located near the front end of the casing 44. This position is indicated in FIG. 1 in broken lines.

The photopolymerizable composition to be dispensed is contained between the plunger 58 and a dispensing opening 29 which is closed by a cap 18. The casing 44, the plunger 58 and the cap 18 are made of opaque material so as to prevent curing of the dental composition within the device. Furthermore the diameter of the dispensing opening 29 is selected to be as small as possible and is typically somewhat less than 1.0 mm, preferably between 0.3 and 0.8 mm. A very narrow dispensing opening 29 is advantageous not only from the viewpoint of obtaining a minimized surface of the composition 30 which is exposed upon removal of the cap 18 but also from the viewpoint of dispensing very finely metered quantities.

The dispensing opening 29 may be formed directly by the front end of the casing 44. As is indicated in broken lines in FIG. 1, however, the tip 34 of the tapering nozzle 17 forming the forward casing end may be formed with a threaded portion 35 which engages with a complementary counter-thread on the nozzle 17. Such an interchangeability of the nozzle tip 34 may be expedient when the device is used by the dentist for dispensing the composition in situ in a patient's mouth.

The rear end of the spindle 46 is formed with a downwardly depending projection 50 which fits into the notch of a guide rail 49 integrally formed with the bottom inner wall of the sleeve 41. An upwardly extending finger 51, which is also provided on the rear end of the spindle 46, extends into an axial slot 52 interrupting the upper wall of the sleeve 41. The projection 50 which runs in the guide rail 49 and the finger 51 which is movable within the longitudinal slot 52 guide the spindle 46 in such a manner that the latter is secured against rotation relative to the sleeve 41 and thus also relative to the handle 61.

The outer surface of the finger 51 which is visible through the axial slot 52 also serves as a level indicator, wherein the outer surface of the sleeve 41 in the vicinity of the axial slot 52 may be provided with a suitable graduation. Lugs 54 are integrally formed on either side face of the finger 51, the upper surfaces of said lugs being of arcuate configuration corresponding to the inner wall of the sleeve 41, whereby an upwardly directed radial yielding of the spindle 46 is prevented. A yielding in the downward direction is prevented by the measure that the spindle 46, or at least its rearward portion carrying the projection 50, runs along the upper edge of the guide rail 49. By these measures it is ensured that also the rear end of the spindle 46 is always centrally guided in axial direction, as is likewise the case with the forward end thereof which is guided by the plunger 58. Therefore no tilting relative to the nut 45 may occur over the entire stroke path of the spindle 46, so that the device will run smoothly in every position.

For use, the device shown in FIG. 1 is held in the right hand such that the handle 61 rests against the ball of the thumb and is surrounded, for instance, by the middle, the fourth and the little fingers. The lower side of the shell 43 will then lie in the bend between thumb and index finger. Thus the device rests securely in the hand, thumb and index finger remaining to be freely movable. When these fingers turn the externally corrugated casing 44, the non-rotatably retained spindle 46 will be moved and thereby push the plunger 58 inside the casing 44 forwardly from the position shown in full lines, so that the dental composition 30 will exit from the dispensing opening 29.

Since it is easier with the described positioning of the hand to rotate the casing 44 by an upward movement of the thumb and a downward movement of the index finger, the nut 45 and the spindle 46 are formed with left-hand threads so that a forward movement of the spindle will be produced in the case of this sense of rotation of the casing 44 and the nut 45.

When the plunger 58 has been fully advanced, the casing 44 will have been emptied as far as possible and will now be discarded together with the spindle 46 and the sleeve 41. Basically, it is possible to re-use the sleeve 41, the spindle 46 and also the nut 45, because these parts will at no time come into contact with the dental composition. But since these component parts may be made of inexpensive plastics materials—like the casing 44, the plunger 58, and the cap 18—it will probably be more economic to discard the entire assembly, which is detachable from the handle 61, when the available dental composition has been dispensed.

Mounting of the assembly, which consists of the casing 44, the plunger 58, the nut 45, the spindle 46, and the sleeve 41, is normally effected by the manufacturer of the dental composition. The casing 44, which is filled with the composition 30 and is closed by the plunger 58, is first pushed into the nut 45. Then the spindle 46 is inserted by screwing it through the nut 45 until the extension 47 is in engagement with the recess 48 formed in the plunger 58. Thereupon the front end of the sleeve 41 is pushed onto the rear end of the casing 44 until the annular ring 45 latches into the annular groove 53. In order to permit ready insertion of the spindle 46 into the sleeve 41 in such a way that the finger 51 provided on the rear end of the spindle will enter the axial slot 52, the guide rail 49 terminates at a distance from the forward end of the sleeve and starts with an inwardly rising ramp 57. In the assembled condition, the finger 51 will appear in the full-line position of FIG. 1 at the rearmost end of the axial slot 52.

A marker cap 60 is pushed into the rear end of the sleeve 41, said cap by its colour or other indication characterizing the dental composition contained in the casing 44.

The dispensing device described above is intended particularly for dental compositions. The same device may be used also for the metered dispensing of other compositions.

We claim:

1. A dispenser for metering dental compositions, comprising
   (a) a casing with a dispensing opening,
   (b) a plunger movable within said casing, the space defined between the plunger and said dispensing opening serving to accommodate the dental composition,
   (c) a threaded spindle which acts on said plunger and is axially movable relative to said casing,
   (d) a nut fixed to said casing and being rotatable relative to said spindle for advancing the same,
   (e) a sleeve member surrounding said spindle and including means for supporting said spindle non-rotatably but axially movably and means for retaining said casing rotatably but axially not movably, and
   (f) a handle detachably joined to said sleeve member.

2. The dispenser of claim 1, wherein said handle comprises a shell partially enclosing said sleeve member, said sleeve member snap-engaging with the shell so as to be secured against rotation and displacement.

3. The dispenser of claim 1, including an axially extending guide rail provided on the inner wall of said sleeve member, said rail cooperating with a non-circular portion of said spindle.

4. The device of claim 3, wherein at a location opposite to said guide rail, said spindle is guided such that radial yielding is prevented.

5. The device of claim 1, wherein said spindle cooperates with said sleeve member to form means for indicating the level of the dental composition in said casing.

6. The device of claim 5, wherein said level indicating means comprises a finger disposed at the rear end of said spindle, the finger being visible through an axially extending slot formed in said sleeve member.

7. The device of claim 6, wherein said axially extending slot and said finger guide said spindle in the axial direction.

8. The device of claim 3, wherein said guide rail commences at a distance behind the front end of said sleeve member with a ramp rising from the outside towards the inside.

9. The device of claim 1, wherein said casing and sleeve member are substantially of circular cylindrical shape and have the same outer diameter.

10. The device of claim 1, wherein the forward end of said spindle is adapted to be coupled to said plunger by means of plug-in connection.

11. The device of claim 1, wherein said nut is fixedly connected to said casing in the axial direction and in the direction of rotation, and is retained relative to said sleeve member by direct engagement of said casing in said sleeve member.

12. The device of claim 11, wherein said nut is adapted to be secured to said casing by displacement transversely to the axial direction.

13. The device of claim 1, wherein said nut and spindle are provided with lefthand threads.

14. The device of claim 1, wherein said casing comprises a funnel-like nozzle constituting the dispensing opening, the minimum inner diameter of said nozzle being less than about 1.0 mm.

15. The device of claim 14, wherein the minimum inner diameter of said nozzle is between 0.3 and 0.8 mm.

16. The device of claim 14, wherein the front part of said nozzle is interchangeable.

* * * * *